United States Patent [19]

Hall

[11] 4,032,296

[45] June 28, 1977

[54] ELECTROLYTIC CONDUCTIVITY DETECTOR SYSTEM

[75] Inventor: Randall C. Hall, West Lafayette, Ind.

[73] Assignee: Purdue Research Foundation, West Lafayette, Ind.

[22] Filed: Jan. 12, 1976

[21] Appl. No.: 648,517

Related U.S. Application Data

[62] Division of Ser. No. 425,116, Dec. 17, 1973, Pat. No. 3,934,193.

[52] U.S. Cl. .................. 23/253 PC; 23/254 E; 23/232 C; 73/23.1; 324/30 B
[51] Int. Cl.$^2$ ............. G01N 27/42; G01N 31/08; G01N 31/12
[58] Field of Search ............... 324/30 B; 23/253 R, 23/253 A, 230 PC, 254 E, 255 E, 232 C; 73/23.1

[56] References Cited

UNITED STATES PATENTS

| | | | |
|---|---|---|---|
| 2,221,307 | 11/1940 | Christie | 324/30 |
| 2,810,879 | 10/1957 | Cade et al. | 324/30 |
| 3,854,881 | 12/1974 | Cohen | 23/253 PC |

Primary Examiner—R.E. Serwin

Attorney, Agent, or Firm—John R. Nesbitt

[57] ABSTRACT

An electrolytic conductivity detector system is disclosed that is particularly useful for gas chromatography. Small gas molecules that will support conductivity are conducted to a gas-liquid contactor where the gas is mixed with a solvent to form a heterogeneous gas-liquid mixture. The gas-liquid mixture is thereafter directed to a gas-liquid separator and a conductivity cell where liquid phase is separated from gas phase and separated liquid phase utilized for conductivity measurement. A unitized gas-liquid separator-conductivity cell may be utilized that includes an inner electrode tube extending upwardly into a larger diameter bore of a metallic outer electrode block, the portion between the block and upper portion of the tube forming a liquid phase reservoir with the liquid phase in the reservoir being utilized for conductivity measurement while between the two electrodes. Three alternate embodiments of a unitized separator-conductivity cell are also disclosed as is a gas-liquid separator and separate conductivity cell. The overall system is small and compact, yet rugged, and is particularly well suited for selective detection of nitrogen, halogen and sulfur containing compounds, although not being limited thereto.

11 Claims, 18 Drawing Figures

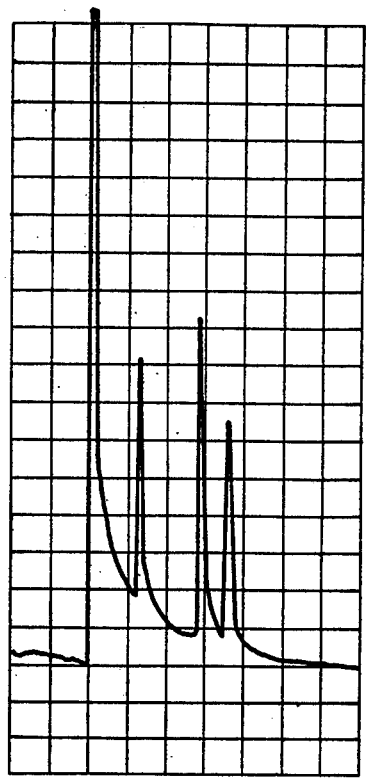
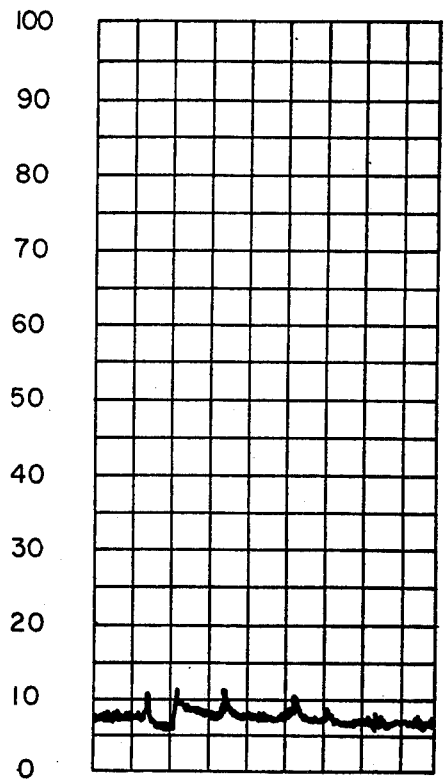
Fig.13A   Fig.13B
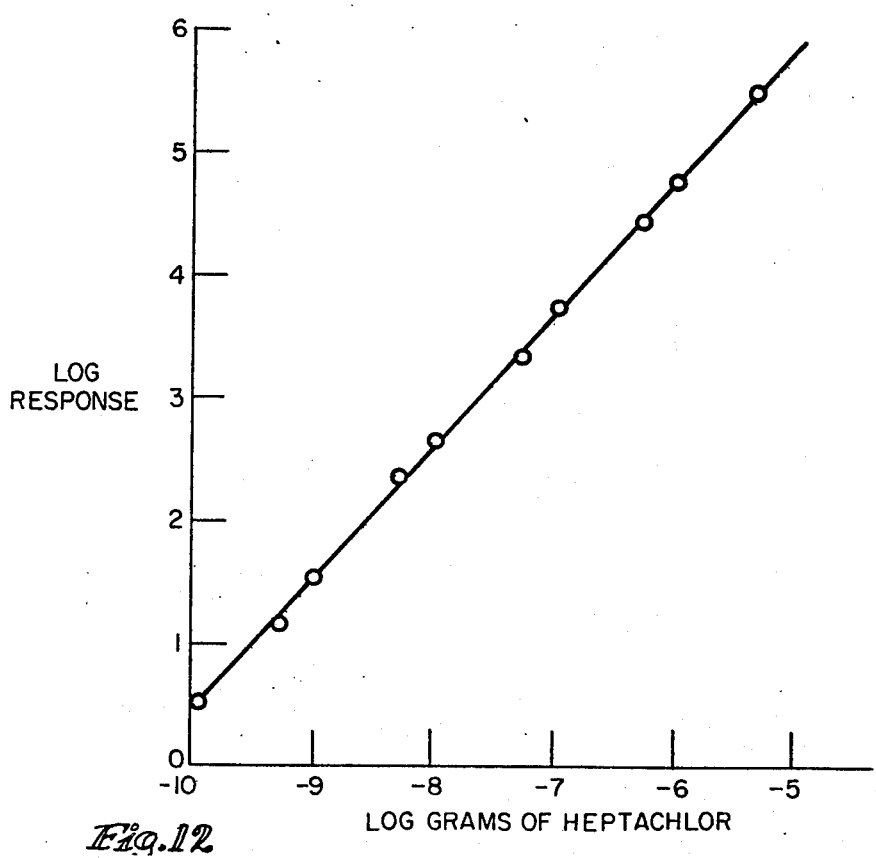
Fig.12   LOG GRAMS OF HEPTACHLOR

ELECTROLYTIC CONDUCTIVITY DETECTOR SYSTEM

RELATED APPLICATION

This application is a division of my copending U.S. Pat. application Ser. No. 425,116, filed Dec. 17, 1973, and entitled "Electrolytic Conductivity Detector", which application issued as U.S. Pat. No. 3,934,193 on Jan. 9, 1976.

FIELD OF THE INVENTION

This invention relates to an electrolytic conductivity detector system and more particularly to an electrolytic conductivity detector system for gas chromatography.

DESCRIPTION OF THE PRIOR ART

The application of electrolytic conductivity for the determination of gas chromatographic eluates has been reported by O. Piringer and M. Pascalau in the Journal of Chromatography, Volume 8, page 410, 1962. In this reported application, organic compounds were combusted to $CO_2$ in a furnace containig CuO, the $CO_2$ dissolved in deionized water in a long capillary tube, and the conductivity of the resulting solution monitored. The sensitivity of the detector was specified to be between that of thermal conductivity and flame ionization detectors.

A detection system similar to that mentioned immediately hereinabove has also been used by D. MM. Coulson, as reported in the Journal of Gas Chromatography, Volume 3, page 134, 1965, for the selective detection of halogen, nitrogen, and sulfur containing compounds. The detector designed by Coulson, unlike the Piringer and Pascalau detector, was designed to give a low response to carbon containing compounds, and the sensitivity achieved was approximately 1-5 ng for polyhalogenated pesticides.

An electrolytic conductivity detector for the determination of chlorine, nitrogen, and sulfur compounds has also been recently described by P. Jones and G. Nickless in the Journal of Chromatography, Volume 73, page 19, 1972. The detector described by Jones and Nickless includes components similar to that of the detector described by Coulson, but utilizes a commercially available conductivity cell and conductivity meter that was originally designed for monitoring liquid or ion-exchange chromatography columns to achieve the conductivity measurements. In addition, the detector utilized was unlike that of the Coulson detector is that it employed a specially prepared nickel catalyst for the reduction of chlorine, nitrogen, and sulfur compounds to HCl, $HN_3$, and $H_2S$, respectively, and a dilute HCl solution was used as the conductivity solvent for monitoring Cl and N compounds. Halogenated compounds were detected by an increase in conductivity, whereas nitrogen compounds were detected by a decrease in conductivity. A dilute reactive EtOH—$I_2$—HCl solution was used for the detection of sulfur containing compounds ($H_2S + I_2 \rightarrow S + 2HI$). Sensitivity to the halogenated compounds was found to be approximately ten times that of the Coulson detector, but sensitivities to nitrogen and sulfur compounds were found to be similar to that of the Coulson detector.

A conductivity detector based on a modified flame ionization detector has also been described in the prior art by J. C. Sternberg and D. T. L. Jones at the Pittsburg Conference of Analytical Chemistry and Applied Spectroscopy, at Cleveland, Ohio, Mar. 5 through 9, 1970.

Besides the selective determination of compounds containing a specific element, electrolytic conductivity detectors have also been used heretofore, at moderate furnace temperatures, for the determination of certain compounds containing the same elements. For example, an electrolytic conductivity detector as designed by Coulson has been utilized heretofore for the selective determination of chlorinated hydrocarbon insecticides in the presence of polychlorinated biphenyls, the achieved selectivity being reported as $>10^4$, with a furnace temperature of 710° C and no reaction gas (See J. W. Dolan, R. C. Hall and T. M. Todd, J. Ass. Office, Anal. Chem., Vol. 55, page 537, 1972), and the same type detector has also been utilized with a furnace temperature of 400°-600° C for the selective detection of N-nitrosamines in the presence of other nitrogen compounds (See J. W. Rhoades and D. E. Johnson, J. Chromtogr. Sci., Vol. 8, page 616, 1970).

SUMMARY OF THE INVENTION

This invention provides an electrolytic conductivity detector that is small and compact yet is rugged and is suitable for gas chromatography. Small molecules that will support conductivity are mixed in a gas-liquid contactor with a solvent after which liquid phase is separated with conductivity measurement of separated liquid phase then occurring. A unitized separator-conductivity cell is preferably utilized to provide separation and conductivity measurement. Enhanced sensitivity and versatility, as well as compactness and simplicity of design and construction, are provided.

It is therefore an object of the invention to provide an improved electrolytic conductivity detector.

It is another object of this invention to provide an improved electrolytic conductivity detector that is small and compact yet is rugged.

It is still another object of this invention to provide an improved electrolytic conductivity detector that is suitable for gas chromatography.

it is yet another object of the invention to provide an improved electrolytic conductivity detector that has enhanced sensitivity and versatility.

It is still another object of this invention to provide an improved electrolytic conductivity detector that has simplicity of design and construction.

It is yet another object of this invention to provide an improved electrolytic conductivity detector that has an improved electrolytic conductivity detector with an improved gas-liquid separator.

It is still another object of this invention to provide an improved electrolytic conductivity detector that has an improved gas-liquid separator wherein the liquid phase is separated prior to conductivity measurement.

It is yet another object of this invention to provide an improved electrolytic conductivity detector having a unitized gas-liquid separator and conductivity cell.

With these and other objects in view, which will become apparent to one skilled in the art as the description proceeds, this invention resides in the novel construction, combination, and arrangement of parts substantially as hereinafter described and more particularly defined by the appended claim, it being understood that such changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 12 is a graph illustrating detector response (peak height) versus grass of heptachlor;

FIGS. 13A and B are graphs illustrating comparison of microelectrolytic conductivity and flame photometric response to sulfur containing compounds.

DESCRIPTION OF THE INVENTION

Figure 1:
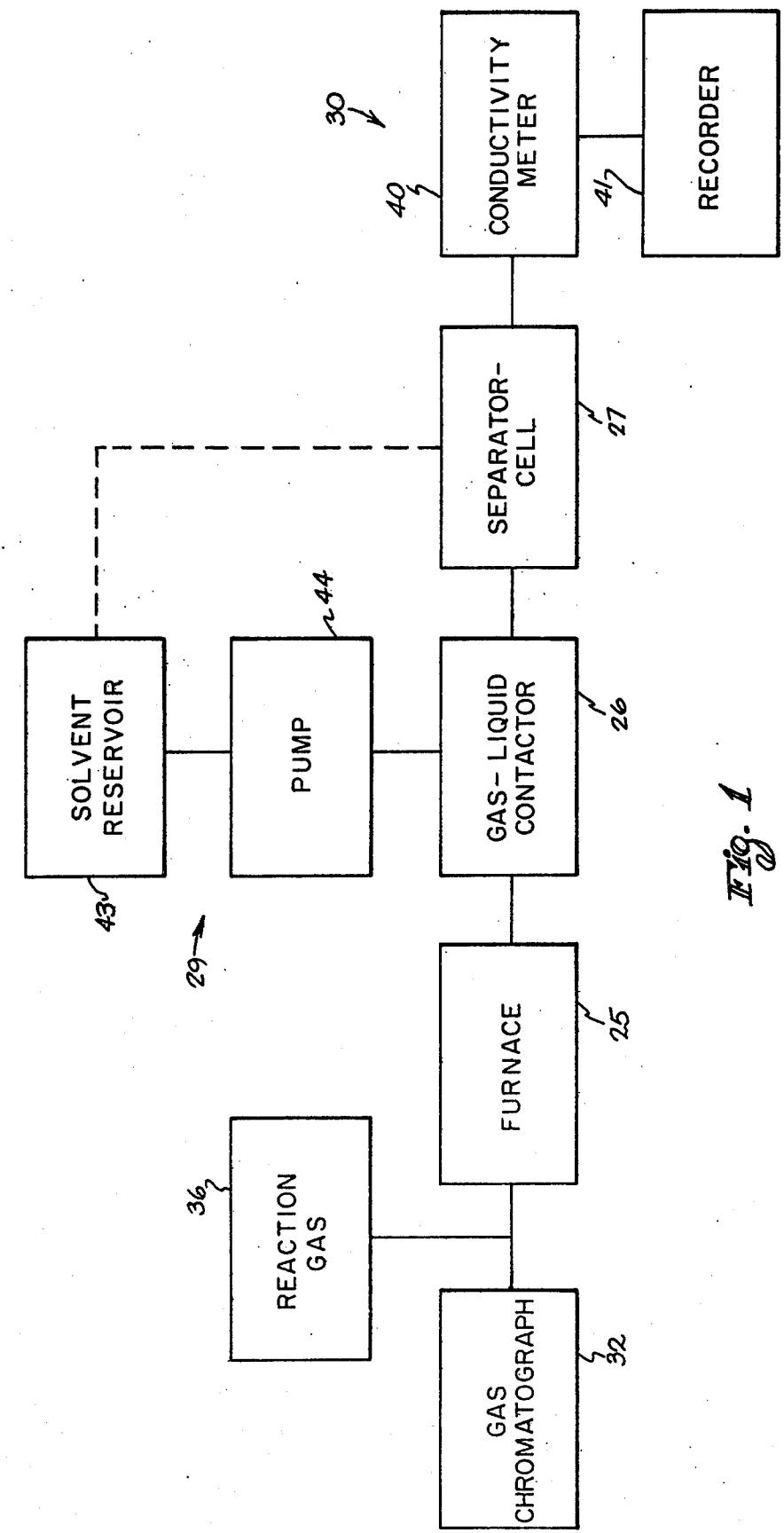
FIG. 1 is a block diagram of the electrolytic conductivity detector system of this invention.

As shown in the block diagram in FIG. 1, the system for the gas chromatograph electrolytic conductivity detector may include a furnace 25 (or other device for the formation of compounds that will support electrolytic conductivity), a gas-liquid contactor 26, a unitized gas-liquid separator-conductivity cell 27, a solvent delivery system 29, and electrical components 30 for measuring conductivity. In this type of detection system, a compound is transferred from a supply source, such as from a gas chromatograph 32, for example, to the furnace where it is degraded to small inorganic compounds that will support electrolytic conductivity, such as, for example, HCl, $SO_3$, $NH_3$, or $CO_2$. As also shown in FIG. 1, gas from an appropriate reaction gas source 36 may be utilized to carry the compound to furnace 25, and the gas reaction source is preferably connected to furnace 25 through a conventional valve (not shown).

The small gaseous molecules are transported from furnace 25 to gas-liquid contractor 26, preferably through glass or Teflon capillary tubing. At gas-liquid contractor 26, the molecules are mixed either with an aqueous or organic solvent. The gas and liquid phases are then conducted to gas-liquid separator-conductivity cell 27 where the liquid phase is separated from any insoluble gases with the collected liquid phase being then utilized for measurement of the electrolytic conductivity. As will be readily appreciated, the unitized separator-conductivity cell functions by having the separator also serve as a concentric electrode conductivity cell. In the unitized separator-cell, the heterogenous gas-liquid mixture from the gas-liquid contractor separates into two smooth flowing homogeneous phases when the mixture comes into contact with the inside wall of the detector block of the separator-cell. The liquid phase then flows down the wall as a sheath with the gas phase as the core. In so doing, the liquid phase passes between the inside wall of the detector block (outer electrode) and the outside wall of the inner gas exit tube (inner electrode) of the separator-cell, with the phases then being finally vented through the gas exit tube. Thus, the driving forces that make the separator-cell function are the bonding attraction between the liquid phase and detector surface, the downward forces of the moving liquid phase, and the positive pressure on the liquid phase in the detector. The principal force responsible for separation of the gas-liquid mixture is the bonding attraction between the liquid phase and the separator surfaces. By the liquid phase adhering to the separator surfaces, the gases are forced to separate from the liquid phase and formed into a gaseous core that is vented from the detector. The stated remaining forces that make the separator-cell function, namely the downward forces of the moving liquid phase and the positive pressure on the liquid phase of the detector cause the liquid phase to flow between the inner and outer electrodes. The positive pressure on the liquid phase is due to the continuous flow of liquid and gas phases into the detector, while the bonding attraction is the result of the materials used. The bonding attraction of the liquid phase to the separator surfaces is thought to be the result of known forces such as van der Walls and hydrogen bonding. With metal used for the separator surfaces and with organic solvents used, van der Walls forces are thought to be more important while hydrogen bonding is thought to play a significant role in the case of a polar liquid such as water used along with moderately polar separator surfaces such as glass. Hence materials and geometry are important, and metal surfaces seen superior to glass, which, in turn, is superior to most plastics in achieving separation (glass is superior to metal, however, for separation of gas and water mixtures).

Specificity in electrolytic conductivity detectors can be achieved by reaction gas composition, reaction temperature, use of abstractors, and conductivity solvent. In the oxidative mode, $SO_2$-$SO_3$, HCl, $CO_2$, $H_2O$, and $N_2$ are the products produced from compounds containing sulfur, chlorine, or nitrogen. Water and $N_2$ give little or no response, $SO_2$ and $SO_3$ can be removed by a CaO Scrubber in the furnace tube, HCl can be removed by a $AgNO_3$ scrubber, and the response due to $CO_2$ can be made negligible by a very short gas-liquid contact time or the use of a nonaqueous solvent. In the reductive mode, $H_2S$, HCl, $NH_3$, and $CH_4$ are the products obtained from organic compounds containing sulfur, chlorine, or nitrogen. Hydrogen sulfide has too weak of an ionization constant to give an appreciable response, HCl can be removed by an acid scrubber such as $Sr(OH)_2$, and the formation of $NH_3$ requires a catalyst. Consequently, by the proper choice of conditions high specificity can be achieved for either sulfur, halogen or nitrogen compounds.

As shown in FIG. 1, measurement of conductivity at conductivity cell 27 can be made by a conventional conductivity meter 40 and the resulting readings at the meter can, if desired, be recorded by a recorder 41 connected conventionally with meter 40.

Solvent circulating system 29 includes a solvent reservoir 43 which receives the solvent passed through the conductivity cell. The liquid is pumped from reservoir 43 by a means of a pump 44, which pump may, for example, be a Teel No. 1P676 centrifugal pump with the solvent from the reservoir being pumped through a bed of Duolite ARM-381 mixed H/OH ion exchange resin (not shown) to gas-liquid contractor 26. A valve (not shown) can be utilized to regulate flow rate.

Figure 2:
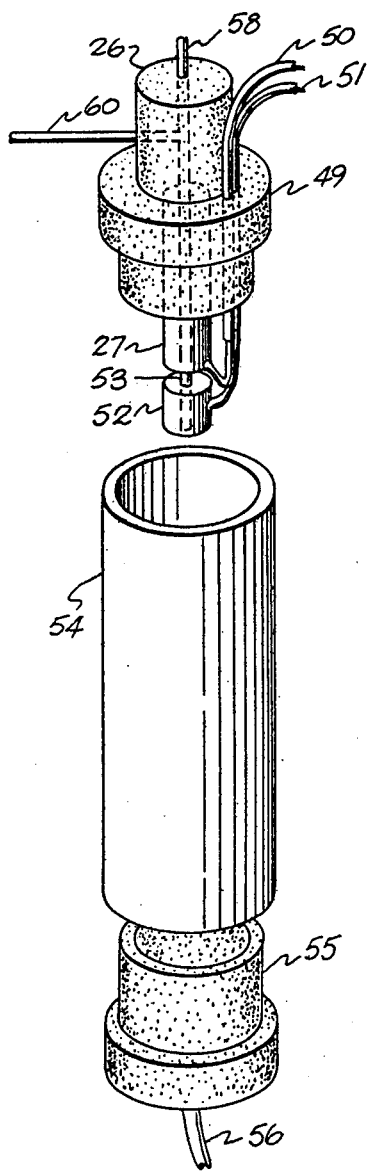
FIG. 2 is an exploded side view of the unitized electrolytic conductivity detector including one embodiment of the unitized separator-conductivity cell.

An exploded view of a portion of the elctrolytic conductivity detector system of this invention is shown in FIG. 2 with one embodiment of the separator-conductivity cell shown. As shown, gas-liquid contractor 26 is mounted to detector cap 49 with gas-liquid separator-conductivity cell 27 being mounted below cap 49. Conductivity cell electrical leads 50 and 51 extend upwardly therefrom through detector cap 49 and are connected with the conductivity meter 40. A brass solvent splatter shield and inner electrode connector 52 is mounted on inner tube and electrode 53. A stainless steel shield and solvent cup 54 fits over the separator-conductivity cell 27 and a reservoir cap 55 is positioned at the bottom of the detector. Cap 55 has a tube 56 extending therefrom connected to inner tube 53 through which solvent is expelled from the detector. The detector, as shown in FIG. 2, is small and compact and need have a diameter no greater than about one inch.

Figure 3:
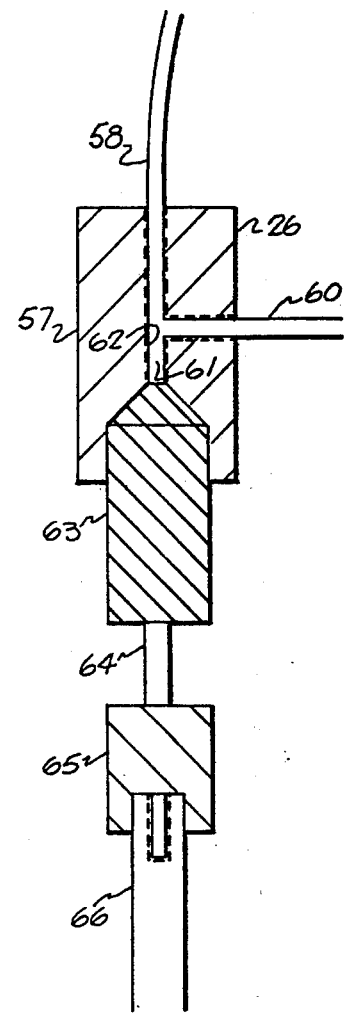
FIG. 3 is a cutaway side view of the preferred embodiment of the unitized separator-conductivity cell of the electrolytic conductivity detector shown in block form in FIG. 1.

FIG. 3 shows a side view of the preferred embodiment of the unitized electrolytic conductivity detector system. As shown, the detector includes a contractor block 57, preferably of Teflon. Block 57 has a bore therein for receiving a solvent delivery tube 58, the bore extending downwardly to the central portion of the block to communicate with a side bore opening to reaction product delivery tube 60. The reaction product delivery bore is preferably of the same dimensions as the solvent delivery bore 58. A solvent-gas delivery passageway 61 extends downwardly from the junction of the inlet bores, the delivery passageway opening into the upper end of the unitized separator-conductivity cell 63 (shown in greater detail in FIG. 5). Solvent delivery passageway 61 is preferably of the same dimensions as the inlet bores. As shown, the unitized separator-conductivity cell 63 has an insulating sleeve 64 extending to an inner electrode connecting block 65 adapted to receive a tube 66 at the lower end through which gas and solvent may be expelled.

Figure 4:
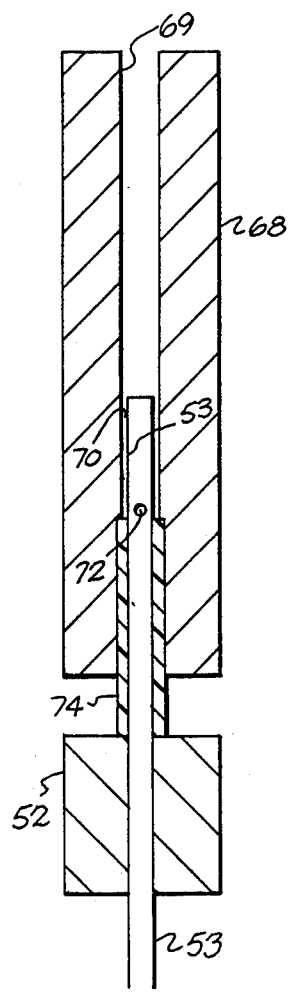
FIG. 4 is a side sectional view of the unitized separator-conductivity cell shown in FIG. 2.

The embodiment of the gas-liquid separator-conductivity cell 27 shown in FIG. 2 is shown in greater detail in FIG. 4. As shown therein, outer electrode and detector block 68 has a bore 69 therein for receiving the gas and liquid mixture from contactor 26. Inner electrode and solvent liquid exit tube 53 extends upwardly and partially into the bore 69. A reservoir 70 is formed between the block 68 and the upper portion of tube 53 with solvent being expelled from the reservoir through aperture 72 in tube 53 near the bottom of the reservoir to allow solvent removal from the separator-conductivity cell 27. Insulating sleeve 74 surrounds tube 53 below reservoir 70 and sleeve 74 preferably extends to the upper edge of connector block 52 through which tube 53 extends and is electrically connected therewith. As can be appreciated from the foregoing, tube 53 (and block 52) and block 68 (inner and outer electrodes) are thus electrically isolated from one another.

In operation the liquid and gas mixture is received in bore 69 from contractor 26. The liquid phase flows downwardly into reserovir 70 where the conductivity measurement is obtained by means of the inner and outer electrodes 53 and 68 (during flow of liquid phase between the electrodes) connected through leads 50 and 51 to conductivity meter 40. The liquid phase is then expelled from the separator-conductivity cell through aperture 72 and tube 53.

Figure 5:
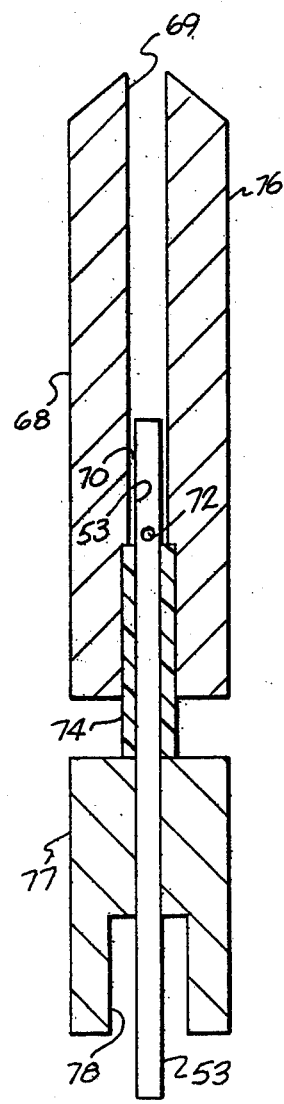
FIG. 5 is a side sectional view of a preferred embodiment of the unitized separator:conductivity cell as shown in FIG. 3.

The preferred embodiment (63 is identified in FIG. 3) of the unitized separator-conductivity cell is shown in detail in FIG. 5. As shown in FIG. 5 the preferred embodiment is like separator-conductivity cell 27 except for modified stainless steel connector blocks 76 and 77. Block 77 preferably engages the lower end of insulating sleeve 74 at the upper edge and has a cylindrical flange 78 extending outwardly from the lower edge, which flange receives a tube or the like such as shown in FIG. 3. Block 76 has a beveled upper edge so as to be received in the mating lower portion of contactor block 57 as shown in FIG. 3. Operation of the preferred embodiment is identical to that as described hereinabove with respect to the embodiment shown in FIGS. 2 and 4.

Figure 6:
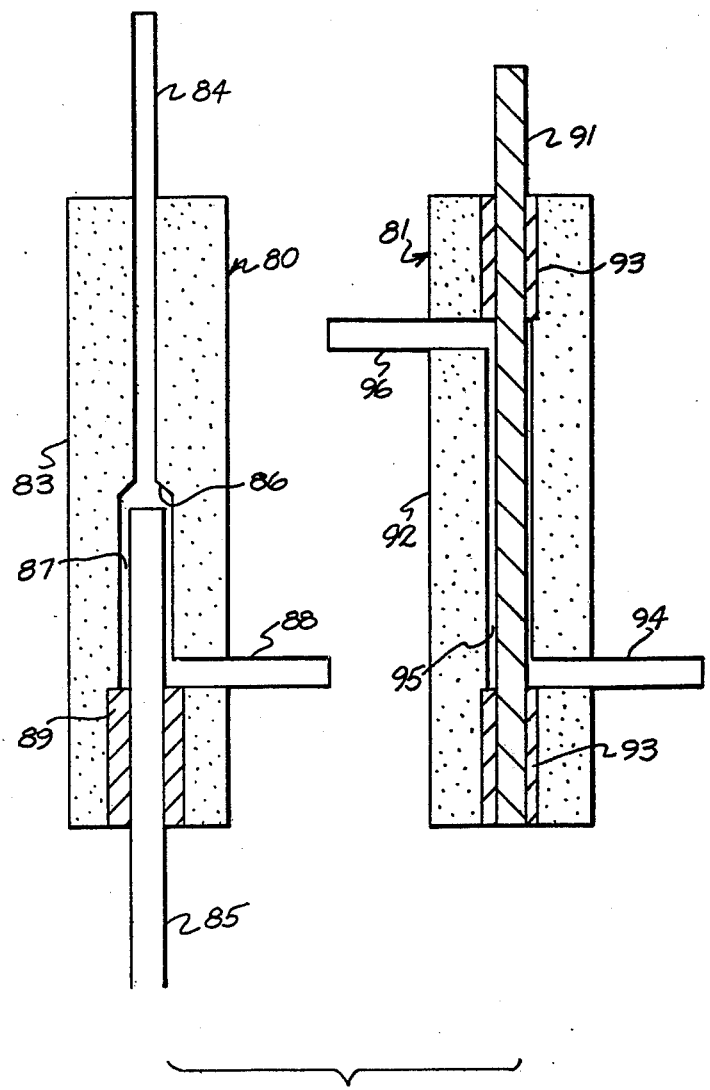
FIG. 6 is an alternate embodiment illustrating a separate separator and a separate conductivity cell in a side sectional view.

A still further alternate embodiment for gas-liquid separator and conductivity measurement is shown in FIG. 6 to consist of a separator 80 and conductivity cell 81. In gas-liquid separator 80, assembly block 83 has an axial bore therethrough, the upper end of which receives solvent-gas delivery tube 84 and may be, for example, a continuation of the solvent-gas delivery tube extending downwardly from gas-liquid contactor 26. Assembly block 183 may be of stainless steel and the axial bore therein has a larger diameter in the lower portion thereof and has an upwardly extending gas exit tube 85 received therein. As shown, tube 85 extends to a point just below a tapered shoulder 86 forming the enlarged portion of the axial bore in the assembly block. Gas exit tube 85 is of smaller diameter than the lower portion of the bore and is preferably 0.0625 inches outside diameter times 0.030 inches internal diameter with the spacing between the gas exit tube and the inner wall of the block 83 forming a small reservoir 87 therebetween (the internal diameter of the bore being preferably 0.0730 inches). A solvent exit tube 88, preferably of Teflon having a 0.0625 inch outside diameter times 0.023 inch internal diameter, is received in a side bore in the assembly block and communicates with the reservoir 87 at or near the bottom thereof. A seal 89, preferably of Teflon, is provided at the bottom of the reservoir extending between the inner wall of the assembly block and the outer wall of gas exit tube 85. The gas and liquid phases enter vertically into the separator 80 through delivery tube 84 and flow down the outside walls and enter vertically into the small reservoir provided between the inner wall of the assembly block and the outer wall of gas exit tube 85. The liquid phase collecting in the reservoir is then withdrawn therefrom through solvent exit tube 88 and conducted to conductivity cell 81.

Conductivity cell 81 is also shown in detail in FIG. 6. As shown therein, a center electrode 91, preferably of 0.0625 inches outside diameter is received within the axial bore of an outer electrode 92 with center electrode 91 being maintained spaced from outer electrode 92 by means of Teflon seals 93 at each end of the cell. Near the lower end of the cell, a side bore in the outer electrode receives solvent entry tube 94, preferably having the same dimensions as solvent exit tube 88 (and connected thereto) of separator 80 and made also of Teflon. Tube 94 supplies liquid phase to passageway 95 in the conductivity cell formed between the center and outer electrodes. A second side bore near the top of the conductivity cell receives solvent exit tube 96 for expelling liquid phase from the conductivity cell, the exit tube being preferably of Teflon and of 0.0625 inch outer diameter times 0.031 inches internal diameter.

Figure 7:
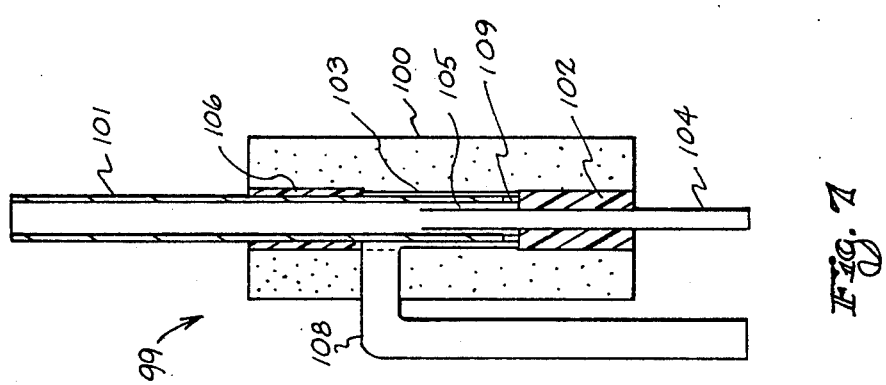
FIG. 7 is a second alternate embodiment of a unitized separator-conductivity cell.

A second alternate embodiment 99 of the unitized separator-conductivity cell is shown in FIG. 7 to include a stainless steel outer electrode and detector housing 100 with a central bore thereon. A gas-liquid inlet and center electrode 101 extends downwardly into the central bore of housing 100 and terminates a short distance above a lower Teflon seal 102 at the bottom portion of the bore to form a passageway 103 between the inner and outer electrodes. A gas exit tube 104 extends upwardly within the bore through lower seal 102 and extends partially within center electrode 101 so as to form a reservoir 105 therebetween. An upper Teflon seal 106 seals the upper end of the passageway 103 formed between the inner and outer electrodes and a side opening exit tube 108 for solvent exit opens from the top of passageway 103 below seal 106.

In operation, embodiment 99 receives the liquid and gas mixture through inlet and center electrode 101. The mixture separates in the tube 101 and a liquid phase is received in reservoir 105 and exits therefrom at the bottom of the reservoir through passageway 109 formed between center electrode 101 and lower seal 102. The liquid phase exiting from the reservoir through passageway 109 is introduced into passageway 103 where it is urged upwardly between the inner and outer electrodes to exit from solvent exit tube 108, the conductivity measurement being made of the liquid phase while in passageway 109.

Figure 8:
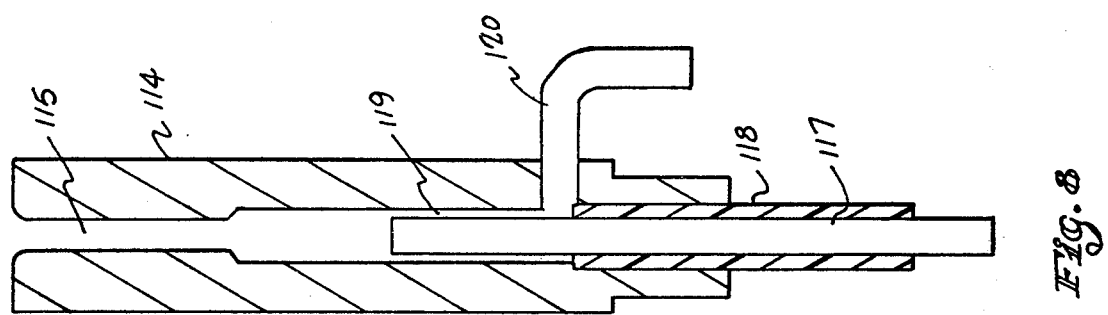
FIG. 8 is a third alternate embodiment of a unitized separator-conductivity cell.

A third embodiment 112 of the unitized separator-conductivity cell is shown in FIG. 8 to include an outer electrode and detector housing 114 having a central bore therein, said bore being of reduced diameter at the top portion 115 to form a gas-liquid inlet. An inner electrode and liquid exit tube 117 extends upwardly into the bore, said inner electrode 117 being maintained spaced from the outer electrode 114 by means of insulating sleeve 118. Inner electrode 117 terminates before the reduced diameter portion 115 of the bore and a reservoir 119 is formed between the inner and outer electrodes. A side-opening exit tube 120 opens from the bottom of the reservoir to allow liquid phase in said reservoir to exit from the separator-conductivity cell. Conductivity measurement is obtained from liquid phae in the reservoir while between the inner and outer electrodes.

As can be seen from the foregoing, the detector system of this invention features extremely small size as compared to heretofore known or utilized electrolytic conductivity detectors and may include a small furnace on the order of 2 inches × 2 inches. This is contrasted, for example, to the detector of Coulson, referenced hereinabove, which utilizes an all glass detector assembly of about 4 inches × 26inches. The detector also includes a gas-liquid separator that will function at any angle including being inverted, has separated 0 to ml quantities of liquid, and is self-starting and maintaining. The detector system also includes the use of an AC conductivity meter with synchronous detection that prevents peak broadening due to polarization effects and provides a linear dynamic range of at least $10^5$. The detector system also allows the use of nonaqueous conductivity solvent (ETOH) which enables the detector to be operated in the oxidative mode without solvent venting and provides a selectivity $>10^5$. The overall design of the detector system of this invention enables the detector assembly to be mounted either at or removed from the furnace and the small size of the furnace allows it to be mounted in any location a standard gas chromatograph detector (i.e. flame ionization) can be mounted.

Figure 9:
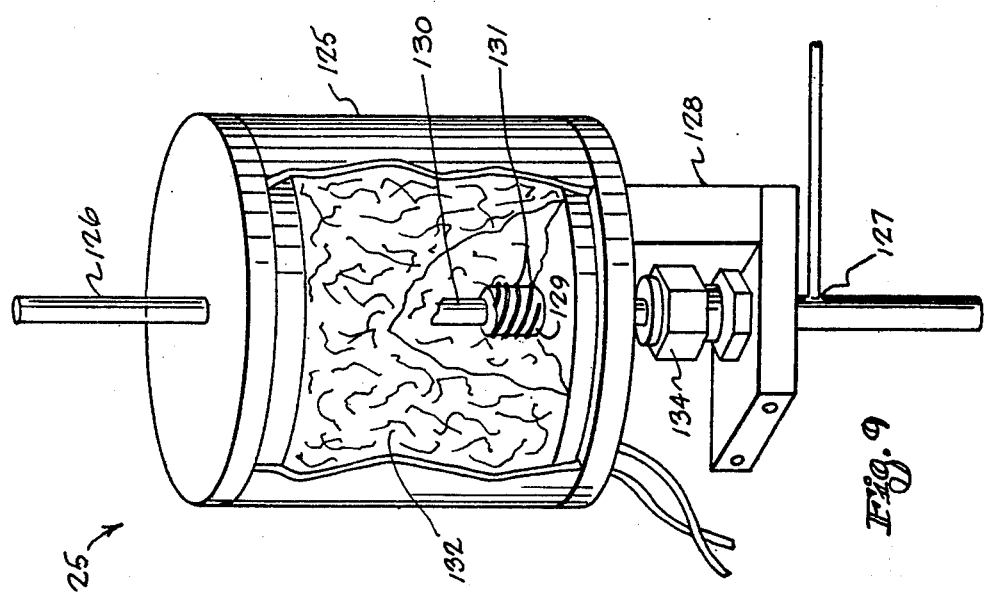
FIG. 9 is a cutaway perspective view of a reaction furnace that may be utilized with this invention.

Furnace 25 is shown in detail in FIG. 9 for illustrative purposes. As shown, furnace 25 includes a furnace housing 125, a quartz reaction tube 126, a reaction gas and column eluant gas entrance tee 127, and a tee mounting device 128. A reaction tube securing device (not shown) can be utilized. The furnace core includes an alumina tube 129 surrounding that portion 130 of quartz reaction tube 126 that is within the furnace with the alumina tube having No. 25 gauge Tophet 30 wire 131 wound thereabout. Insulating filler 132 then surrounds the alumina tube within the furnace. The quartz reaction tube 126 is preferably mounted to the inlet tee by Teflon ferrules (not shown) and secured by a stainless steel nut 134.

Performance of the detector of this invention as shown in FIG. 8, is illustrated in the various graphs and charts of FIGS. 10 through 13. The detector of FIG. 8 was evaluated both in the reductive and oxidative modes using a Chromatronix conductivity meter. The detector furnace was operated at 820° centigrade in the reductive mode and at 840° centigrade in the oxidative mode with 1 cc/min of either hydrogen or oxygen reaction gas. Reaction tubes were 6 mm OD × 0.5 mm ID × 150 mm length quartz tubes and were used empty with no prior conditioning. The detector was mounted on a Tracor MT-220 gas chromatograph and interfaced to the column exit by approximately 6 inches of 1/16 inch stainless steel tubing. For separations in the evaluation of the detector in the oxidative mode, a 6 foot × ¼ foot glass column containing 3% OV-1 and 3% OV-210 on 80/100 mesh Gas Chrom Q qas operated at 215° centigrade with a nitrogen carrier gas flow rate of 40–50 cc/min (for helium a flow rate of 50 cc/min was utilized), with an inlet temperature of 230° centigrade. The conductivity solvent was 95–100% ethyl alcohol. Solvent flow rate through the detector was 0.41 cc/min. For separations in the evaluation of the detector in the reductive mode, a similar glass column on 80/100 mesh acid washed Chromosorb W was utilized with a furnace temperature of 820° centigrade.

Figure 10A:
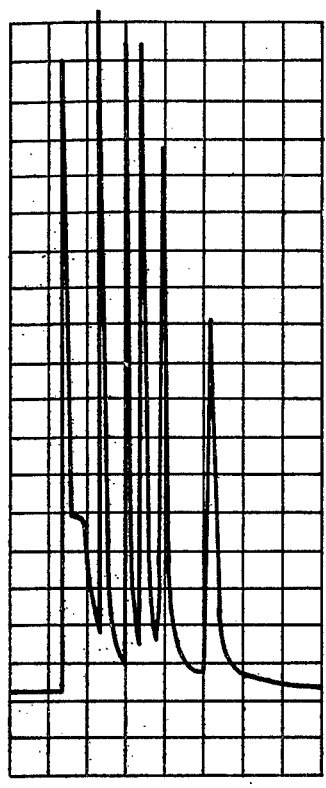
FIGS. 10A through C are graphs illustrating detector response to chlorinated hydrocarbon pesticides in the reductive mode.
Figure 10B:
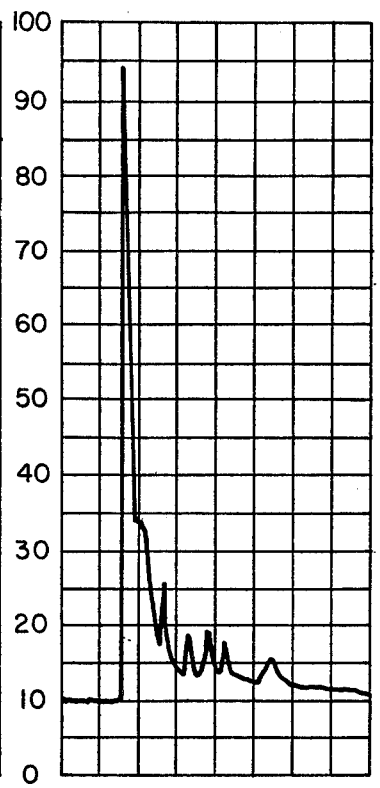
Figure 10C:
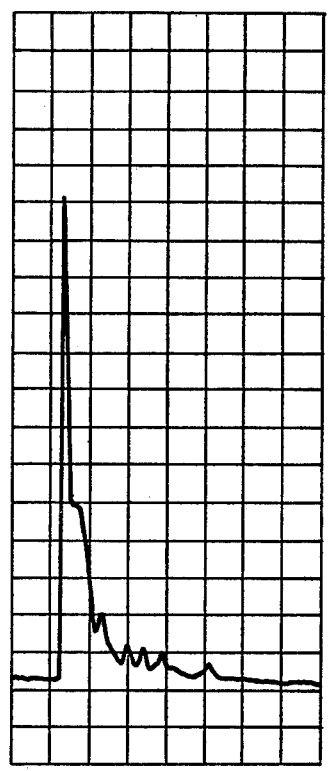
Figure 11A:
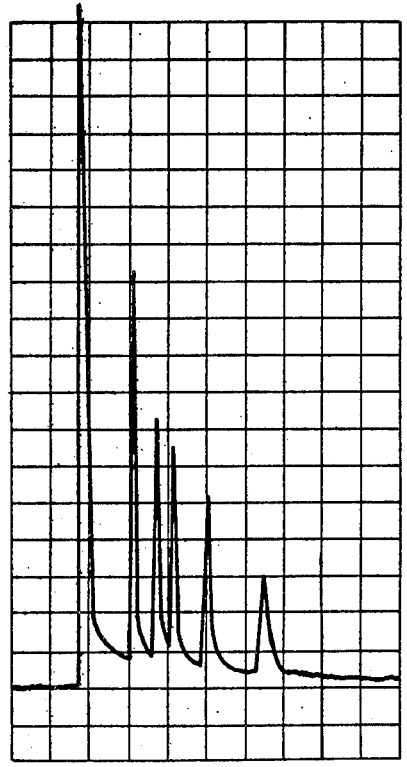
FIGS. 11A and B are graphs illustrating detection response to chlorinated hydrocarbon pesticides in the oxidative mode.
Figure 11B:
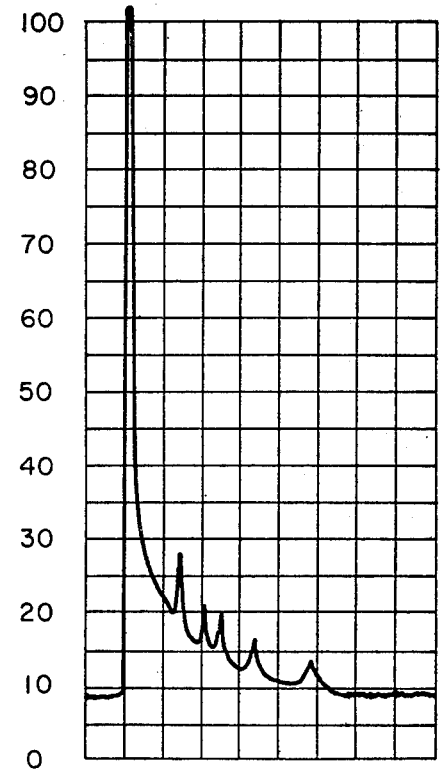

Detector response to chlorinated hydrocarbon pesticides in the reductive mode for 1 ng (FIG. 10A 0.1 ng (FIG. 10B), and 0.05 ng (FIG. 10C) of lindane, heptachlor, aldrin, heptachlor epoxide, and dieldrin, in order of elution, with a detector sensitivity of 0.2 $\mu$mho/mv. Detector response for same pesticides in the oxidative mode is shown for 1 ng with detector sensitivity of 0.4 $\mu$mho/mv (FIG. 11A) and 0.1 ng with detector sensitivity of 0.2 $\mu$mho/mv (FIG. 11B).

As can be seen from these illustrations, the detector of this invention exhibits high sensitivity and stability, the detector being much more sensitive than heretofore known detectors such as, for example, the Coyulson electrolytic conductivity detector. Selectivity (relative to hydrocarbon) is also extremely high. Detector response (peak height) versus grams of heptachlor is shown in FIG. 12.

A comparison of microelectrolytic conductivity and flame photometric responses to sulfur containing compounds is shown in FIG. 13. The order of elution is diazinon, malathion, and parathion with FIG. 13A showing the electrolytic conductivity detector and FIG. 13B showing the flame photometric detector. The electrolytic conductivity detector of this invention gives approximately 50% full scale deflection at 0.5% noise for 5 ng od diazinon, malathion, and parathion. In contrast, the flame photometric detector of the prior art gives only about 2% to 3% deflection at twice the noise level for the same quantity of compound. The electrolytic conductivity detector of this invention has high sensitivity to sulfur compounds and has wide linear dynamic range (the flame photometirc detector's response is exponential with concentration) making it an attractive device for the analysis of sulfur containing pesticides and air pollutants.

Figure 14:
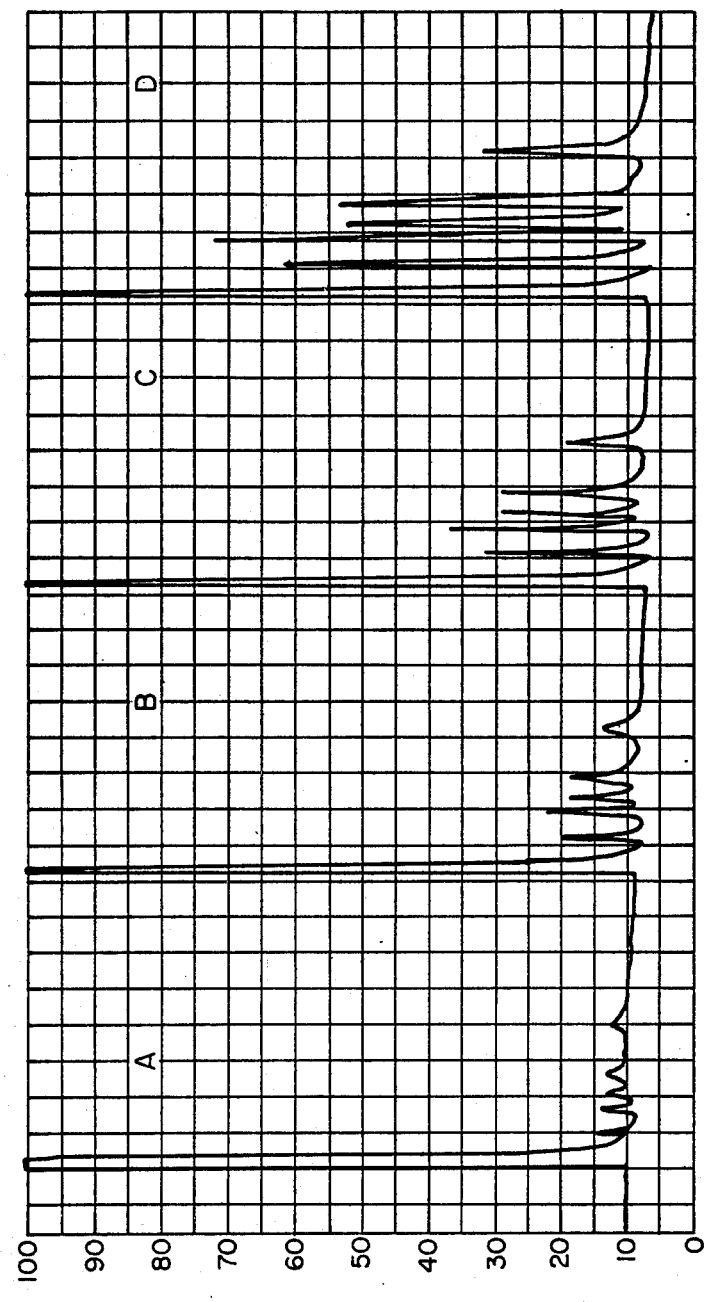
FIGS. 14A, B, C and D are graphs illustrating detector response identifying the preferred embodiment of the separator-conductivity cell.

Detector response for the preferred embodiment shown in FIGS. 3 and 5 has been found to be at least as good as that shown for the detector in FIG. 8 as set forth hereinabove, and in many instances better. The graphs of FIG. 14 illustrate performance of the detector utilizing the preferred embodiment of the separator-conductivity cell shown in FIGS. 3 and 5. Detector response to chlorinated hydrocarbon pesticides in the reductive mode is shown, for illustrative purposes in FIG. 14. A Tracor 550 as chromotograph was used, as were coiled glass columns with the same packing as described hereinabove in conjunction with the detector system producing the response indicated by the graphs as shown in FIGS. 10–13. The column temperature was 185° centigrade and helium carrier gas was used at a flow rate of 30 ml/mi. The furnace was operated at 850° centigrade with ~/cc/min $H_2$ reaction gas. The quartz tube utilized was 3 mm O.D. × 1 mm I.D. times 100 mm long, and solvent flow was 0.15 ml/min ETOH with a sensitivity of 0.2 $\mu$mho/mv. Detector response is shown to chlorinated hydrocarbon pesticides in the reductive mode for 0.02 ng (FIG. 14A), 0.05 ng (FIG. 14B), 0.1 ng (FIG. 14C), and 0.2 ng (FIG. 14D) of lindane, heptachlor, aldrin, heptachlor epoxide, and dieldrin, in order of elution.

From the foregoing, it can be seen that the electrolytic conductivity detector of this invention provides an improved detector having a separator and conductivity cell. The gas-liquid separator-conductivity cell is felt to operate on a different principle than known prior detectors in that the geometry and principle of operation as utilized in the detector of this invention allows the dimensions to be easily altered as desired. The ability of the detector of this invention to utilize small quantities of solvent is advantageous because the sensitivity of detecting devices such as conductivity cell is inversely proportional to the quantity of solvent utilized. This is shown to be a further advantage of this invention since utilized quantities of solvent may be as low as 0.15 ml per minute while prior art devices required utilization of a minimum of 3 to 5 ml of water per minute, which can result in a 20 to 30 fold increase in sensitivity of the electrolytic conductivity detector of this invention.

Thus, the electrolytic conductivity detector of this invention gives high performance, is easy to use, and is of small size and enables easy mounting. In addition, since the detector has high sensitivity, it is more useful than known devices of this type. Since the detector also has high selectivity and wide linear dynamic range, the detector is more useful in many instances than is the electron capture detector. Finally, the detector requires little maintenance and can be used trouble-free for long periods of time.

The gas-liquid separator-conductivity cell makes the detector capable of high performance and small size. The concentric tube separator does not require a minimum solvent flow rate for operation, and since the primary force that drives the solvent through the conductivity cell is the downward force of the moving solvent, solvent flow rate through the cell approaches zero as the total solvent flow rate approaches zero. Thus, the cell is always filled with solvent which prevents bubbles being lodge between the closely spaced electrodes, which is advantageous since the solvent often tends to channel around a bubble rather than displacing it.

The separator-conductivity cell functions efficiently and delivers a smooth solvent flow through the cell with solvent flow rates from 0.1 to 1.0 cc/min and gas flow rates from 5 to 500 cc/min or more.

What is claimed is:

1. An electolytic conductivity detector for gas chromatography, said detector comprising:
   compound supply means for providing as an output therefrom compounds to be tested in the form of eluant gases;
   forming mans for receiving said eluant gases from said compound supply means and forming therefrom conductivity supporting inorganic gaseous molecules;
   solvent supply means for supplying an aqueous or organic solvent;
   contactor means for mixing substantially immediately upon contact gaseous molecules received from said forming means with said solvent from said solvent supply means to form a mixture thereof;
   separator means for receiving said mixture from said contactor means and substantially immediately separating said mixture into liquid and gas phases; and
   measuring means for receiving said liquid phase from said separator means and measuring the conductivity of said liquid phase.

2. The electrolytic conductivity detector of claim 1 wherein said detector is of small size with said contactor means, said separator means, and said measuring means being assembled as a single unit.

3. The electrolytic conductivity detector claim 1 wherein said forming means is a furnace having an input receiving said eluant gases from said compound supply means for formation of compounds therefrom having small molecules that will support electrolytic conductivity, and wherein said detector includes reaction gas supply means also connected with said furnace input.

4. The electrolytic conductivity detector system of claim 1 wherein said measuring means includes a conductivity meter connected with said measuring means.

5. The electrolytic conductivity detector of claim 4 wherein said measuring means also includes a recorder connected with said conductivity meter.

6. The electrolytic conductivity detector of claim 1 wherein said system also includes a solvent circulating system for receiving liquid from said separating and measuring means and supplying solvent to said mixing means.

7. The electrolytic conductivity detector of claim 6 wherein said solvent circulating system includes a solvent reservoir and a pump for withdrawing solvent from said reservoir and for controlling solvent delivery to said mixing means.

8. An electrolytic conductivity detector for gas chromatography, said detector comprising:
   means for forming conductivity supporting molecules of a compound to be tested;
   means for mixing molecules received from said forming means with a solvent to form a mixture;
   means for separating said mixtured into liquid and gas phases, said separating means including a reservoir for receiving said liquid phase;
   a conductivity cell;
   means for conducting said liquid phase from the reservoir of said separating means through said conductivty cell; and
   means for measuring the conductivity of said liquid withdrawm from the reservoir of said separating means and passing through said conductivity cell.

9. The electrolytic conductivity detector of claim 8 wherein said separating means and said conductivity cell are mounted in contiguous side by side positions, and wherein said system includes a rugged housing for protecting siad separating means and conductivity cell.

10. The electrolytic conductivity detector of claim 9 wherein said housing is cylindrical and of a size no greater than about one inch in diameter and two inches in length.

11. An electrolytic detector for gas chromatography, said detector comprising:
   a furnace for forming conductivity supporting gaseous molecules of a compound to be tested;
   a solvent supply means supplying an aqueous or organic solvent;
   a gas-liquid contactor means for receiving said molecules from said furnace and solvent from said solvent supply means and substantially immediately mixing the same to form a mixture thereof;
   a gas-liquid separator and conductivity measuring cell for receiving said mixture from said contactor means and substantially immediately separating the same into liquid and gas phases and measuring the conductivity of said liquid phase, said separator and measuring cell including a reservoir for receiving said liquid phase to measured; and
   means for indicating the conductivity of liquid phase while in said separator and conductivity cell as sensed at said conductivity measuring cell.

* * * * *

REEXAMINATION CERTIFICATE (621st)
United States Patent [19]
Hall

[11] B1 4,032,296
[45] Certificate Issued    Jan. 20, 1987

[54] ELECTROLYTIC CONDUCTIVITY DETECTOR SYSTEM

[75] Inventor: Randall C. Hall, West Lafayette, Ind.

[73] Assignee: Purdue Research Foundation, West Lafayette, Ind.

Reexamination Request:
No. 90/000,828, Jul. 30, 1985

Reexamination Certificate for:
Patent No.: 4,032,296
Issued: Jun. 28, 1977
Appl. No.: 648,517
Filed: Jan. 12, 1976

Related U.S. Application Data

[62] Division of Ser. No. 425,116, Dec. 17, 1973, Pat. No. 3,934,193.

[51] Int. Cl.$^4$ .................. G01N 27/08; G01N 30/64; G01N 31/12
[52] U.S. Cl. ......................................... 422/89; 73/23.1; 324/446; 324/448; 324/450; 422/90; 436/101; 436/113; 436/119; 436/133; 436/149; 436/150
[58] Field of Search .................. 422/89, 90; 436/149, 436/150, 161; 324/439, 446, 448, 450

[56] References Cited

U.S. PATENT DOCUMENTS

| | | | |
|---|---|---|---|
| 1,807,821 | 6/1931 | Behr | 324/448 |
| 2,258,045 | 10/1941 | Christie | 324/448 |
| 3,031,272 | 4/1962 | Agerbek-Poulsen et al. | 422/90 |
| 3,111,392 | 11/1963 | Stout, Jr. | 422/90 |
| 3,309,845 | 3/1967 | Coulson . | |

OTHER PUBLICATIONS

Jones, P., and G. Nickless, "Versatile Electrolytic Conductivity Detector for Gas Chromatography," *Journal of Chromatography*, 73:19–28 (1972).

Coulson, Dale M., "Electrolytic Conductivity Detector for Gas Chromatography," *Journal of Gas Chromatography*, 3:134–137 (1965).

Piringer, Otto, Eugen Tataru, and Mircea Pascalau, "Construction and Operation of the Electrolytic Conductivity Detector," *Journal of Gas Chromatography*, 2:104 (1964).

Piringer, Otto and Mircea Pascalau, "Short Communications," *Journal of Chromatography*, 8:410–412 (1962).

Mohnke, M., O. Piringer, and E. Tataru, "Analysis of the Isotope Molecules of Hydrogen Using Capillary Columns and an Electrolytic Conductivity Detector," *Journal of Gas Chromatography*, 6:117 (1968).

*Primary Examiner*—Arnold Turk

[57] ABSTRACT

An electrolytic conductivity detector system is disclosed that is particularly useful for gas chromatography. Small gas molecules that will support conductivity are conducted to a gas-liquid contactor where the gas is mixed with a solvent to form a heterogeneous gas-liquid mixture. The gas-liquid mixture is thereafter directed to a gas-liquid separator and a conductivity cell where liquid phase is separated from gas phase and separated liquid phase utilized for conductivity measurement. A unitized gas-liquid separator-conductivity cell may be utilized that includes an inner electrode tube extending upwardly into a larger diameter bore of a metallic outer electrode block, the portion between the block and upper portion of the tube forming a liquid phase reservoir with the liquid phase in the reservoir being utilized for conductivity measurement while between the two electrodes. Three alternate embodiments of a unitized separator-conductivity cell are also disclosed as is a gas-liquid separator and separate conductivity cell. The overall system is small and compact, yet rugged, and is particularly well suited for selective detection of nitrogen, halogen and sulfur containing compounds, although not being limited thereto.

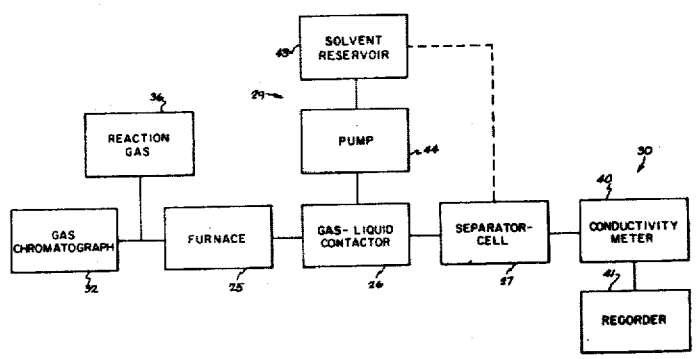

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8–10 are cancelled.

Claims 1 and 11 are determined to be patentable as amended.

Claims 2–7, dependent on an amended claim, are determined to be patentable.

New claims 12–21 are added and determined to be patentable.

1. An electrolytic conductivity detector for gas chromatography, said detector comprising:
   compound supply means for providing as an output therefrom compounds to be tested in the form of eluant gases;
   forming means for receiving said eluant gases from said compound supply means and forming therefrom conductivity supporting inorganic gaseous molecules;
   solvent supply means for supplying an aqueous or organic solvent;
   contactor means for mixing substantially immediately upon contact gaseous molecules received from said forming means with said solvent from said solvent supply means to form a mixture thereof;
   separator means for receiving said mixture from said contactor means and substantially immediately separating said mixture into liquid and gas phases; and
   measuring means for receiving said liquid phase from said separator means and measuring the conductivity of said liquid phase[.];
   *said separator means including an axial bore adapted to permit the liquid phase to flow along its wall with the gas phase flowing as a core; and*
   *said measuring means being located along the bore so as to measure the liquid phase conductivity as the gas phase continues to flow through the bore.*

11. An electrolytic detector for gas chromatography, said detector comprising:
   a furnace for forming conductivity supporting gaseous molecules of a compound to be tested;
   a solvent supply means supplying an aqueous or organic solvent;
   a gas-liquid contactor means for receiving said molecules from said furnace and solvent from said solvent supply means and substantially immediately mixing the same to form a mixture thereof;
   a gas-liquid separator and conductivity measuring cell for receiving said mixture from said contactor means and substantially immediately separating the same into liquid and gas phases and measuring the conductivity of said liquid phase, said separator and measuring cell including *an axial bore adapted to permit the liquid phase to flow along its wall with the gas phase as a core*, a reservoir for receiving said liquid phase to *be* measured, *and measuring means located along the bore for measuring the liquid phase conductivity as the gas phase continues to flow through the bore;* and
   means *coupled to said measuring means* for indicating the conductivity of liquid phase while in said separator and conductivity cell as sensed at said conductivity measuring cell.

*12. The detector of claim 11 wherein said measuring means comprises first and second, concentric electrodes.*

*13. The detector of claim 11 wherein said measuring means comprises an inner electrode tube extending upwardly into a larger diameter bore of an outer electrode.*

*14. The detector of claim 13 wherein the inner and outer electrodes form the reservoir of the cell.*

*15. An electrolytic conductivity detector system comprising:*
   *a gas chromatograph;*
   *forming means for receiving eluant gases from said gas chromatograph and forming therefrom conductivity supporting inorganic gaseous molecules;*
   *solvent supply means for supplying an aqueous or organic liquid solvent;*
   *contactor means for mixing substantially immediately upon contact gaseous molecules received from said forming means with said liquid solvent from said supply means to form a mixture thereof; and*
   *a cell including a detector block having an axial bore for receiving a flow of said mixture from said contactor means and causing the liquid to separate from insoluble gases when the mixture comes into contact with the wall of the bore and flow along the wall with the gas phase continuing to flow through the bore, and including first and second electrodes located along the bore to provide for conductivity measurement of the liquid phase while between the electrodes as insoluble gas continues to flow through the bore.*

*16. An electrolytic conductivity detector system for gas chromatography, said detector system comprising:*
   *a gas chromatograph;*
   *forming means for receiving eluant gases from said gas chromatograph and forming therefrom conductivity supporting inorganic gaseous molecules;*
   *solvent supply means for supplying an aqueous or organic solvent;*
   *contactor means for mixing substantially immediately upon contact gaseous molecules received from said forming means with said solvent from said supply means to form a mixture thereof; and*
   *a detector cell including a block having an axial bore for receiving a flow of said mixture from said contactor means and causing the liquid to separate from insoluble gases when the mixture comes into contact with the wall of the bore and flow along the wall with the gas continuing to flow through the bore, and first and second, spaced-apart electrodes disposed along the bore and each having a surface portion thereof exposed to the interior of the bore to provide for conductivity measurement of the flow along the bore while between the electrodes and as insoluble gas continues to flow through the bore.*

*17. An electrolytic conductivity detector for gas chromatography, said detector comprising:* compound supply means for providing as an output therefrom compounds to be tested in the form of eluant gases;

forming means for receiving said eluant gases from said compound supply means and forming therefrom conductivity supporting inorganic gaseous molecules;

solvent supply means for supplying an aqueous or organic solvent;

contactor means for mixing substantially immediately upon contact gaseous molecules received from said forming means with said solvent from said solvent supply means to form a mixture thereof;

separator means for receiving said mixture from said contactor means and substantially immediately separating said mixture into liquid and gas phases; and measuring means for receiving said liquid phase from said separator means and measuring the conductivity of said liquid phase;

said contactor means, separator means, and measuring means being unitized within a detector cell block;

said contactor means having a first inlet bore for receiving said solvent, a second inlet bore in communication with the first bore for receiving said gaseous molecules, and a solvent-gas mixture delivery passageway extending downwardly from the junction of the inlet bores;

said separator means including an axial bore in communication with the solvent-gas mixture delivery passageway for receiving said mixture and adapted to permit the separated liquid phase to flow along its wall with the gas phase flowing as a core; and said measuring means being located along the bore so as to measure the liquid phase conductivity as the gas phase continues to flow through the bore.

18. The detector of claim 17 wherein said measuring means includes first and second electrodes.

19. The detector of claim 17 wherein said measuring means includes first and second, spaced-apart electrodes, each having a surface portion thereof exposed to the interior of the bore.

20. The detector of claim 17 wherein said measuring means includes a pair of concentric electrodes.

21. An electrolytic conductivity detector for gas chromatography, said detector comprising:

compound supply means for providing as an output therefrom compounds to be tested in the form of eluant gases;

forming means for receiving said eluant gases from said compound supply means and forming therefrom conductivity supporting inorganic gaseous molecules;

solvent supply means for supplying an aqueous or organic solvent;

contactor means for mixing substantially immediately upon contact gaseous molecules received from said forming means with said solvent from said solvent supply means to form a mixture thereof;

separator means for receiving said mixture from said contactor means and substantially immediately separating said mixture into liquid and gas phases; and measuring means for receiving said liquid phase from said separator means and measuring the conductivity of said liquid phase;

said separator means and said measuring means being unitized within a detector cell block;

said separator means including an axial bore adapted to permit liquid phase to flow along its wall with the gas phase flowing as a core; and said measuring means being located along the bore so as to measure the liquid phase conductivity as the gas phase continues to flow through the bore.

* * * * *